United States Patent
Freed et al.

(10) Patent No.: US 10,420,338 B2
(45) Date of Patent: Sep. 24, 2019

(54) APPARATUS FOR TESTING, ASSESSMENT, AND MAINTENANCE OF HARVESTED HEARTS FOR TRANSPLANTING

(71) Applicant: TEVOSOL, INC., Edmonton (CA)

(72) Inventors: Darren H. Freed, Edmonton (CA); Paul Mundt, Winnipeg (CA); Ayyaz Ali, Cambridge (GB); Stephen Large, Cambridge (GB); Simon Colah, Cambridge (GB)

(73) Assignee: TEVOSOL, INC., Edmonton, Alberta (CA)

( * ) Notice: Subject to any disclaimer, the term of this patent is extended or adjusted under 35 U.S.C. 154(b) by 154 days.

(21) Appl. No.: 15/622,237

(22) Filed: Jun. 14, 2017

(65) Prior Publication Data

US 2017/0339946 A1    Nov. 30, 2017

Related U.S. Application Data

(63) Continuation of application No. 14/372,909, filed as application No. PCT/CA2013/000031 on Jan. 17, 2013, now Pat. No. 9,706,768.

(60) Provisional application No. 61/587,452, filed on Jan. 17, 2012.

(51) Int. Cl.
*A01N 1/02*    (2006.01)
*A61B 5/0402*    (2006.01)

(52) U.S. Cl.
CPC .......... *A01N 1/0247* (2013.01); *A61B 5/0402* (2013.01)

(58) Field of Classification Search
CPC .................................................. A01N 1/0247
See application file for complete search history.

(56) References Cited

U.S. PATENT DOCUMENTS

| | | | |
|---|---|---|---|
| 5,157,930 | A | 10/1992 | McGhee et al. |
| 5,217,860 | A | 6/1993 | Fahy et al. |
| 5,716,378 | A | 2/1998 | Minten |
| 5,807,737 | A | 9/1998 | Schill et al. |
| 6,046,046 | A | 4/2000 | Hassanein |
| 6,582,375 | B2 | 6/2003 | Melvin et al. |

(Continued)

FOREIGN PATENT DOCUMENTS

| | | |
|---|---|---|
| CA | 2144952 A1 | 3/1994 |
| CA | 2521324 A1 | 10/2004 |

(Continued)

OTHER PUBLICATIONS

Non-final Office Action dated May 31, 2018 in related U.S. Appl. No. 15/128,634.

(Continued)

*Primary Examiner* — Jonathan M Hurst

(57) ABSTRACT

An apparatus, a system, and methods for receiving, perfusing and maintaining and assessing excised donor heart physiological functionality. The system generally comprises an apparatus for receiving and holding an excised heart that is interconnected with: (i) a perfusate-processing system, (ii) a bi-directional perfusate pumping system, (iii) flow sensors for monitoring the flow of perfusate to and from an installed heart's aorta, pulmonary artery, pulmonary vein, and vena cava, (iv) an ECG apparatus interconnectable with the installed heart, and (v) probes interconnecting the installed heart with instruments for monitoring the heart's physiogical functionality using load independent indices and load dependent indices.

18 Claims, 12 Drawing Sheets

(56) References Cited

U.S. PATENT DOCUMENTS

| | | |
|---|---|---|
| 6,953,655 B1 | 10/2005 | Hassanein et al. |
| 7,045,279 B1 | 5/2006 | Laske et al. |
| 7,811,808 B2 | 10/2010 | Van Der Plaats et al. |
| 8,585,380 B2 | 11/2013 | Hassanein et al. |
| 9,706,768 B2 | 7/2017 | Freed et al. |
| 2001/0018569 A1 | 8/2001 | Erbel et al. |
| 2004/0248281 A1 | 12/2004 | Wright et al. |
| 2005/0255442 A1 | 11/2005 | Brassil et al. |
| 2006/0154358 A1 | 7/2006 | Hassanein et al. |
| 2007/0009881 A1 | 1/2007 | Arzt et al. |
| 2007/0098694 A1 | 5/2007 | Khuri et al. |
| 2008/0017194 A1 | 1/2008 | Hassanein et al. |
| 2010/0028850 A1 | 2/2010 | Brassil |
| 2011/0129810 A1 | 6/2011 | Owen et al. |
| 2011/0177487 A1 | 7/2011 | Simsir et al. |
| 2012/0183945 A1 | 7/2012 | Steen |
| 2012/0282591 A1 | 11/2012 | Thatte et al. |
| 2012/0330438 A1 | 12/2012 | Keshavjee et al. |
| 2013/0157248 A1 | 6/2013 | Fishman et al. |
| 2013/0295552 A1 | 11/2013 | Hassanein et al. |
| 2014/0220550 A1 | 8/2014 | Van Der Plaats et al. |
| 2015/0017710 A1 | 1/2015 | Freed et al. |
| 2016/0113269 A1 | 4/2016 | Woodard et al. |

FOREIGN PATENT DOCUMENTS

| | | |
|---|---|---|
| CA | 2861545 A1 | 7/2013 |
| DE | 102005048625 A1 | 4/2007 |
| EP | 2809153 | 12/2014 |
| EP | 3229588 | 10/2017 |
| WO | 2013106908 A1 | 7/2013 |
| WO | 2015143552 A1 | 10/2015 |

OTHER PUBLICATIONS

Examination Report No. 1 dated Apr. 27, 2018 in related Australian Patent Application No. 2015234580.
Written Opinion dated Mar. 15, 2016 in PCT/CA2015/051316.
International Search Report dated Mar. 16, 2016 in PCT/CA2015/051316.
International Preliminary Report on Patentability (IPRP) dated Apr. 10, 2017 in PCT/CA2015/051316.
International Preliminary Report on Patentability dated Sep. 27, 2016 in PCT/CA2015/050201.
Office Action dated Apr. 4, 2016 in related Canadian Patent Application No. 2,861,545.
Supplementary European Search Report dated Jan. 25, 2016 in EP Patent Application No. 13738530.
International Preliminary Report on Patentability dated Apr. 23, 2014 in PCT/CA2013/000031.
International Search Report dated Jun. 10, 2015 in PCT/CA2015/050201.
De Hart, et al., "An ex vivo platform to simulate cardiac physiology: a new dimension for therapy development and assessment", The International Journal of Artificial Organs, Jun. 2011, pp. 495-505, vol. 34, No. 6.
Tipton, et al., "The use of Langendorff preparation to study the bradycardia of training", Medicine and Science in Sports, vol. 9, No. 4, pp. 220-230 (1977).
International Search Report received in PCT Application No. PCT/CA2013/000031 dated Apr. 15, 2013.
Written Opinion received in PCT Application No. PCT/CA2013/000031 dated Apr. 15, 2013.
Written Opinion received in PCT/CA2015/050201 dated Jun. 10, 2015.
Non-final Office Action dated Jan. 8, 2016 in related U.S. Appl. No. 14/372,909.
Final Office Action dated Jul. 12, 2016 in related U.S. Appl. No. 14/372,909.
Non-final Office Action dated Jan. 20, 2017 in related U.S. Appl. No. 14/372,909.
Notice of Allowance dated Apr. 11, 2017 in related U.S. Appl. No. 14/372,909.
Communication from European Patent Office in related EP Patent Application No. 13738530.8 dated Nov. 21, 2017.
Extended European Search Report dated Nov. 30, 2017 in EP Patent Application No. 15767752.7.
Search Report dated Sep. 3, 2018 in related EP Patent Application No. 15867786.4.
Final Office Action dated Oct. 11, 2018 in related U.S. Appl. No. 15/128,634.
Search Report dated Feb. 8, 2019 in related EP Patent Application No. 15867786.4.
Notice of Allowance dated Feb. 8, 2019 in related U.S. Appl. No. 15/128,634.
Examination Report No. 1 dated Mar. 19, 2019 in related Australian Patent Application No. 2015361996.

APPARATUS FOR TESTING, ASSESSMENT, AND MAINTENANCE OF HARVESTED HEARTS FOR TRANSPLANTING

CROSS-REFERENCE TO RELATED APPLICATIONS

This application is a continuation of U.S. patent application Ser. No. 14/372,909, filed on Jul. 17, 2014, entitled "APPARATUS FOR TESTING, ASSESSMENT, AND MAINTENANCE OF HARVESTED HEARTS FOR TRANSPLANTING", which is a national filing of PCT International Application No. PCT/CA2013/000031, filed Jan. 17, 2013, entitled "APPARATUS FOR TESTING, ASSESSMENT, AND MAINTENANCE OF HARVESTED HEARTS FOR TRANSPLANTING", which claims benefit of, and priority from, U.S. Provisional Patent Application No. 61/587,452, filed Jan. 17, 2012, the entire contents of each of which are incorporated herein by reference.

FIELD OF THE INVENTION

The present invention pertains to apparatus, systems, and methods for ex vivo perfusion and maintenance of harvested donor hearts, and more particularly, to pre-transplant assessment of harvested donor hearts for their suitability for transplantation.

BACKGROUND OF THE INVENTION

Heart failure affects 10% of North Americans and is the leading hospital discharge diagnosis. The diagnosis of heart failure is accompanied by a survival outlook that is comparable to a major cancer. There are limited rehabilitation options available to patients who are suffering with heart failure, and few strategies actually re-power the heart. Cardiac transplantation remains the gold-standard therapeutic intervention for patients with end-stage heart failure, with an increasing number of individuals being added to the transplant wait list every year. However, wider application of this life-preserving intervention is limited by the availability of donors. Data from the International Society of Heart and Lung Transplantation Registry shows that cardiac transplantation is in progressive decline in suitable donors (2007, *Overall Heart and Adult Heart Transplantation Statistics*). Two hundred and fifty eight Canadians have died during the last decade (2000-2010; Heart and Stroke Foundation of Canada) while waiting for heart transplantation. Similarly, in the United States, 304 patients died in 2010 alone while waiting for heart transplantation (Organ Procurement and Transplantation Network, US Dept. of Health & Human Services). This phenomenon is primarily due to a shortage of suitable organ donors, and is being experienced across the globe.

Time is of the essence for removal of a heart from a donor and its successful transplantation into a recipient. The following principles generally apply for optimal donor heart preservation for the period of time between removal from the donor and transplantation: (i) minimization of cell swelling and edema, (ii) prevention of intracellular acidosis, (iii) prevention of injury caused by oxygen free radicals, and (iv) provision of substrate for regeneration of high-energy phosphate compounds and ATP during reperfusion. The two main sources of donor hearts for transplantation are breathing patients who have suffered irreversible loss of brain function as a result of blunt head trauma or intracerebral hemorrhage and are classified as "brainstem-dead" donors, and patients who have suffered circulatory death and are referred to as "non-heart-beating" donors.

Brainstem-dead organ donors can be maintained under artificial respiration for extended periods of time to provide relative hemodynamic stability up throughout their bodies until the point of organ retrieval. Therefore, cardiac perfusion is uncompromised and organ functionality is theoretically maintained. However, brainstem death itself can profoundly affect cardiac function. The humoral response to brainstem death is characterized by a marked rise in circulating catecholamines Physiological responses to this "catecholamine storm" include vasoconstriction, hypertension and tachycardia, all of which increase myocardial oxygen demand. In the coronary circulation significant increased levels of catecholamine circulating throughout the vascular system induce vasoconstriction which in turn, compromises myocardial oxygen supply and can lead to subendocardial ischemia. This imbalance between myocardial oxygen supply and demand is one factor implicated in the impairment of cardiac function observed following brainstem death (Halejcio-Delophont et al., 1998, Increase in myocardial interstitial adenosine and net lactate production in brain-dead pigs; an in vivo microdialysis study. Transplantation 66(10):1278-1284; Halejcio-Delophont et al, 1998, Consequences of brain death on coronary blood flow and myocardial metabolism. Transplant Proc. 30(6):2840-2841). Structural myocardial damage occurring after brainstem death is characterized by myocytolysis, contraction band necrosis, sub-endocardial hemorrhage, edema and interstitial mononuclear cell infiltration (Baroldi et al., 1997, Type and extent of myocardial injury related to brain damage and its significance in heart transplantation: a morphometric study. J. Heart Lung Transplant 16(10):994-1000). In spite of no direct cardiac insult, brainstem-dead donors often exhibit reduced cardiac function and the current views are that only 40% of hearts can be recovered from this donor population for transplantation.

Well-defined criteria have been developed for harvesting organs for transplantation from non-heart-beating donors (Kootstra et al., 1995, Categories of non-heart-beating donors. Transplant Proc. 27(5):2893-2894; Bos, 2005, Ethical and legal issues in non-heart-beating organ donation. Transplantation, 2005. 79(9): p. 1143-1147). Non-heart-beating donors have minimal brain function but do not meet the criteria for brainstem death and therefore, cannot be legally declared brainstem dead. When it is clear that there is no hope for meaningful recovery of the patient, the physicians and family must be in agreement to withdraw supportive measures. Up to this point in care, non-heart-beating patients are often supported with mechanical ventilation as well as intravenous inotropic or vasopressor medication. However, only those with single system organ failure (neurologic system) can be considered for organ donation. Withdrawal of life support, most commonly the cessation of mechanical ventilation, is followed by anoxic cardiac arrest after which, the patient must remain asystolic for five minutes before organ procurement is allowed. Consequently, non-heart-beating donors are necessarily exposed to variable periods of warm ischemia after cardiac arrest which may result in various degrees of organ damage. However, provided that the time duration of warm ischemia is not excessive, many types organs, i.e., kidneys, livers, and lungs, harvested from non-heart-beating donors are able to recover function after transplantation with success rates that approximate those for transplanted organs from brainstem-dead beating donors.

Numerous perfusion apparatus, systems and methods have been developed for ex vivo maintenance and transportation of harvested organs. Most employ hypothermic conditions to reduce organ metabolism, lower organ energy requirements, delay the depletion of high energy phosphate reserves, delay the accumulation of lactic acid, and retard morphological and functional deteriorations associated with disruption of oxygenated blood supply. Harvested organs are generally perfused in these systems with preservative solutions comprising antioxidants and pyruvate under low temperatures to maintain their physiological functionality. However, it has been found that increasing amounts of free radicals and catalytic enzymes are produced during extended maintenance of harvested organs in pulsing pressurized hypothermic systems. Fluctuating perfusion pressures in such systems can damage the organs by washing off their vascular endothelial lining and traumatize the underlying tissues. Furthermore, the harvested organs will elute increasing amounts of intracellular, endothelial and membrane constituents resulting in their further physiological debilitation.

The short-comings of hypothermic apparatus, systems and methods have been recognized by those skilled in these arts, and alternative apparatus, systems and methods have been developed for preservation and maintenance of harvested organs at temperatures in the range of about 25° C. to about 35° C., commonly referred to as "normothermic" temperatures. Normothermic systems typically use perfusates based on the Viaspan formulation supplemented with one or more of serum albumin as a source of protein and colloid, trace elements to potentiate viability and cellular function, pyruvate and adenosine for oxidative phosphorylation support, transferrin as an attachment factor; insulin and sugars for metabolic support, glutathione to scavenge toxic free radicals as well as a source of impermeant, cyclodextrin as a source of impermeant, scavenger, and potentiator of cell attachment and growth factors, a high $Mg^{++}$ concentration for microvessel metabolism support, mucopolysaccharides for growth factor potentiation and hemostasis, and endothelial growth factors (Viaspan comprises potassium lactobionate, $KH_2PO_4$, $MgSO_4$, raffinose, adenosine, glutathione, allopurinol, and hydroxyethyl starch). Other normothermic perfusation solutions have been developed and used (Muhlbacher et al., 1999, Preservation solutions for transplantation. Transplant Proc. 31(5):2069-2070). While harvested kidneys and livers can be maintained beyond twelve hours in normothermic systems, it has become apparent that normothermic bathing, and maintenance of harvested hearts by pulsed perfusion beyond 12 hours results in deterioration and irreversible debilitation of the hearts' physiological functionality. Another disadvantage of using normothermic continuous pulsed perfusion systems for maintenance of harvested hearts is the time required to excise the heart from a donor, mount it into the normothermic perfusion system and then initiate and stabilize the perfusion process. After the excised heart has been stabilized, its physiological functionality is determined and if transplantation criteria are met, then the excised heart is transported as quickly as possible to a transplant facility.

SUMMARY OF THE INVENTION

The present disclosure pertains to an apparatus, a system, and methods for receiving, perfusion, maintenance and pre-transplant assessment of the physiological functionality of an excised donor heart. The system generally comprises an apparatus for receiving and holding an excised heart that is interconnected with: (i) a perfusate-processing system, (ii) a bi-directional perfusate pumping system, (iii) flow sensors for monitoring the flow of perfusate to and from an installed heart's aorta, pulmonary artery, pulmonary vein, and vena cava, (iv) an ECG apparatus interconnectable with the installed heart, and (v) probes interconnecting the installed heart with instruments for monitoring the heart's physiological functionality using load independent indices and load dependent indices.

BRIEF DESCRIPTION OF THE DRAWINGS

The present invention will be described in conjunction with reference to the following drawings in which.

DESCRIPTION OF THE INVENTION

Figure 1:
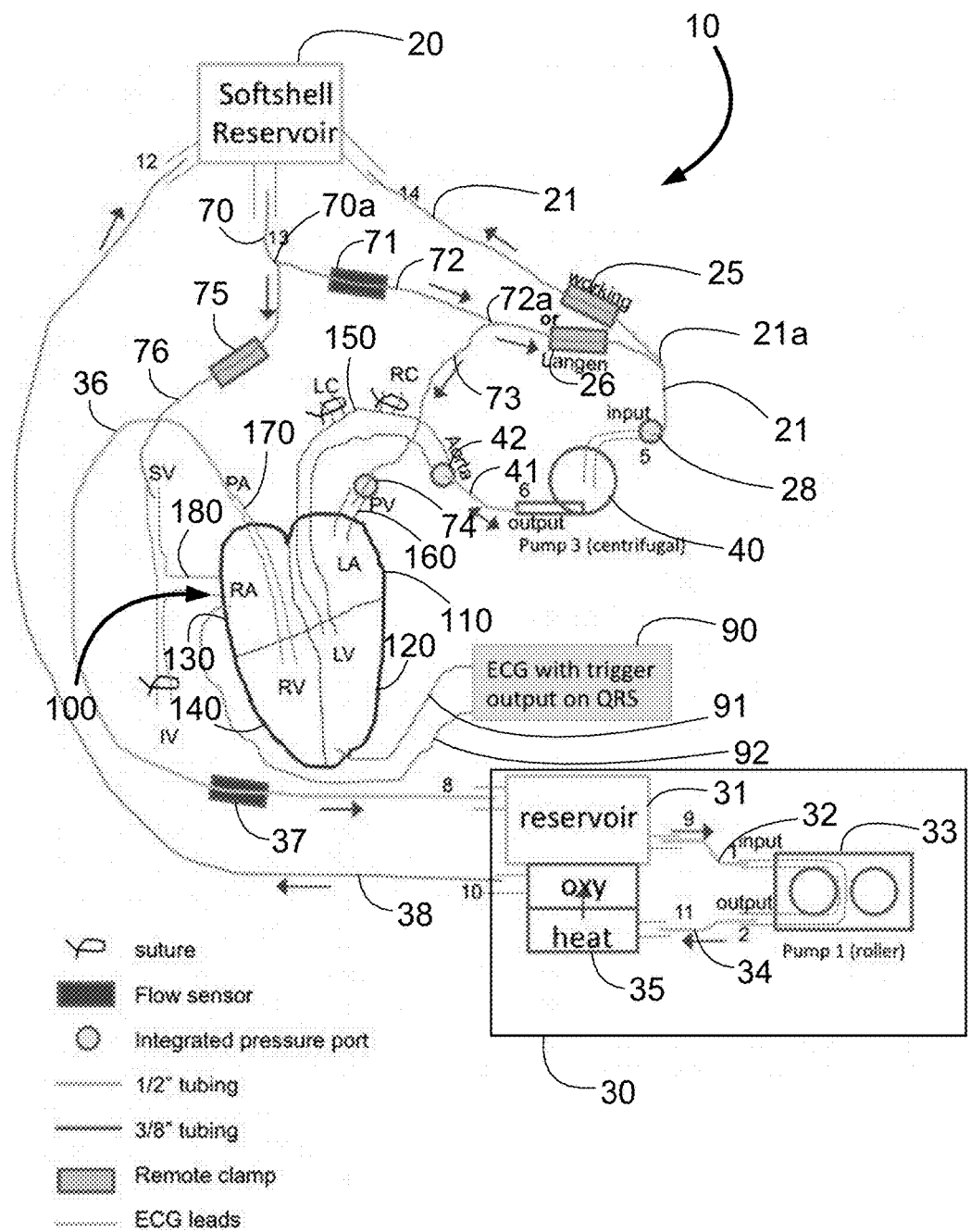
FIG. 1 is a schematic illustration of an exemplary testing, assessment, and maintenance apparatus for harvested donor hearts, according to one embodiment of the present disclosure.

Unless otherwise defined, all technical and scientific terms used herein have the same meaning as commonly understood by one of ordinary skill in the art to which this invention belongs. In order that the invention herein described may be fully understood, the following terms and definitions are provided herein.

The word "comprise" or variations such as "comprises" or "comprising" will be understood to imply the inclusion of a stated integer or groups of integers but not the exclusion of any other integer or group of integers.

The term "about" or "approximately" means within 20%, preferably within 10%, and more preferably within 5% of a given value or range.

The term "afterload" means the mean tension produced by a chamber of the heart in order to contract. It can also be considered as the 'load' that the heart must eject blood against. Afterload is therefore a consequence of aortic large vessel compliance, wave reflection and small vessel resistance (left ventricular afterload) or similar pulmonary artery parameters (right ventricular afterload).

The term "preload" refers to the stretching of a single cardiac myocyte immediately prior to contraction and is therefore related to the sarcomere length.

Since sarcomere length cannot be determined in the intact heart, other indices of preload such as ventricular end diastolic volume or pressure are used. As an example, preload increases when venous return is increased.

The term "cardiac myocyte" means a cardiac muscle cell.

The term "stroke volume" (SV) means the volume of blood ejected by the right/left ventricle in a single contraction. It is the difference between the end diastolic volume (EDV) and the end systolic volume (ESV). Mathematically, SV=EDV−ESV. The stroke volume is affected by changes in preload, afterload and inotropy (contractility). In normal hearts, the SV is not strongly influenced by afterload whereas in failing hearts, the SV is highly sensitive to afterload changes.

The term "stroke work" (SW) refers to the work performed by the left or right ventricle to eject the stroke volume into the aorta or pulmonary artery, respectively. The area enclosed by the pressure/volume loop is a measure of the ventricular stroke work, which is a product of the stroke volume and the mean aortic or pulmonary artery pressure (afterload), depending on whether one is considering the left or the right ventricle.

The term "ejection fraction" (EF) means the fraction of end diastolic volume that is ejected out of the ventricle during each contraction. Mathematically, EF=SV/EDV. Healthy ventricles typically have ejection fractions greater than 0.55. Low EF usually indicates systolic dysfunction and severe heart failure can result in EF lower than 0.2. EF is also used as a clinical indicator of the inotropy (contractility) of the heart. Increasing inotropy leads to an increase in EF, while decreasing inotropy decreases EF.

The term "end systolic pressure volume relationship" (ESPVR) describes the maximal pressure that can be developed by the left ventricle at any given left ventricular volume, or alternatively, by the right ventricle at any given right ventricular volume. This implies that the PV loop cannot cross over the line defining ESPVR for any given contractile state. The slope of ESPVR (Ees) represents the end-systolic elastance, which provides an index of myocardial contractility. The ESPVR is relatively insensitive to changes in preload, afterload and heart rate. This makes it an improved index of systolic function over other hemodynamic parameters like ejection fraction, cardiac output and stroke volume.

The ESPVR becomes steeper and shifts to the left as inotropy (contractility) increases. The ESPVR becomes flatter and shifts to the right as inotropy decreases.

The term "preload recruitable stroke work relationship" (PRSW) means a measure of cardiac contractility, and is the linear relationship between SW and EDV.

The term "pressure-volume area" (PVA) means the total mechanical energy generated by ventricular contraction. This is equal to the sum of the stroke work (SW), encompassed within the PV loop, and the elastic potential energy (PE). Mathematically, PVA=PE+SW.

The term "Langendorff perfusion" refers to a method of perfusing an excised heart with a nutrient-rich oxygenated solution in a reverse fashion via the aorta. The backwards pressure causes the aortic valve to shut thereby forcing the solution into the coronary vessels, which normally supply the heart tissue with blood. This feeds nutrients and oxygen to the cardiac muscle, allowing it to continue beating for several hours after its removal from the animal.

The term "working heart" as used herein, refers to clinical ex vivo coronary perfusation throughout a excised heart by ventricular filling via the left atrium and ejection from the left ventricle via the aorta driven by the heart's contractile function and regular cardiac rhythm. The excised heart is attached by cannulae to a perfusate reservoir and circulatory pumps in a Langendoff preparation. The flow of perfusate through the excised heart in "working heart" mode is in the direction opposite to the flow of perfusate during Langedorff perfusion.

The term "ischemia" means a condition that occurs when blood flow and oxygen are kept from the heart.

The term "conduit" as used herein means cannula.

The present disclosure pertains to apparatus, systems and methods for assessing excised hearts after delivery to transplantation facilities, to determining their suitability for transplantation, and for maintaining selected excised hearts until transplantation.

One exemplary embodiment of the present disclosure relates to an apparatus for receiving, maintaining and assessing an excised donor heart under continuous Langendorff perfusion and periodic "working heart" perfusion mode. The exemplary apparatus generally comprises a hard-shell container, a removable support for positioning and retaining an excised heart, removable soft-shell reservoir for a perfusate, and a lid sealably engagable with the hard shell container. The lid is provided with a plurality of ports for sealable engaging conduits for interconnecting: (i) the soft-shell reservoir with a supply of heated and oxygenated perfusate, (ii) the soft-shell reservoir with an output pump, (iii) the excised heart with a perfusion cannula inserted into its aorta, (iv) the excised heart with a perfusion cannula inserted into its pulmonary artery, (v) the excised heart with a perfusion cannula inserted into its pulmonary vein, (vi) the excised heart with a perfusion cannula inserted into its vena cava, and (vii) the excised heart with a cannula inserted into its vena cava for delivery of non-perfusate solutions. The lid may also be provided with ports for probes and leads for attachment to the cannulae and/or heart. Alternatively, the ports for the probes and leads may be integrally provided on a surface of the hard-shell reservoir.

Another exemplary embodiment of the present disclosure relates to a system for receiving, perfusing and maintaining and assessing an excised donor heart. The system generally comprises the above-disclosed apparatus interconnected with: (i) a perfusate-processing system, (ii) a bi-directional perfusate pumping system, (iii) flow sensors for monitoring the flow of perfusate to and from an installed heart's aorta, pulmonary artery, pulmonary vein, and vena cava, (iv) an ECG apparatus interconnectable with the installed heart, and (v) probes interconnecting the installed heart with instruments for monitoring the heart's physiological functionality using load independent indices and load dependent indices. Suitable perfusate-processing systems are exemplified by heart-lung machines commonly used for coronary bypass surgeries.

Another exemplary embodiment of the present disclosure relates to methods for: (i) maintaining an installed excised heart while preserving its physiological functionality by continuous Langendorff perfusion at normothermic temperatures ranging from about 24° C. to about 35° C., and (ii) assessing the installed excised heart for transplantation under forward perfusion flow using load independent indices exemplified by left ventricular end systolic pressure volume relationships, right ventricular end systolic pressure volume relationships, left ventricular preload recruitable stroke work relationships, right ventricular preload recruitable stroke work relationships, and isovolumic relaxation constants measured as Tau. The methods disclosed herein may incorporate measurements and assessments of load dependent indices in combination with the load independent indices. Suitable load dependent indices are exemplified by diastolic blood pressure, systolic blood pressure, mean blood pressure, among others. The methods disclosed herein for use with the apparatus and system of the present disclosure can utilize perfusion solutions known by those skilled in these arts, to be useful for perfusion of excised hearts. Suitable perfusion solutions are exemplified by whole blood, whole blood amended with citrate and/or phosphate and/or dextrose, modified Krebs solutions, Viaspan, modified Viaspan solutions, and the like.

An exemplary use of the apparatus, system and methods of the present disclosure generally comprises the steps of selection, preparation, and balancing of a perfusate solution, setting up the system by interconnecting the perfusate-processing system and the bi-directional perfusate pumping system with cannulae that are subsequently interconnected with the appropriate ports on the lid of the receiving, maintaining, and assessing apparatus, priming the interconnected system with the perfusate solution, installing an excised heart onto the support provided with the apparatus and then installing the appropriate cannulae into the heart's aorta, pulmonary artery, pulmonary vein, and vena cava, expressing all air from within the heart and the cannulae, and then commencing the Langendorff perfusion at a normothermic temperature from the range of about 25° C. to about 35° C.

It should be noted that the levels of haematocrit, $Ca^{++}$, $K^+$, $NaHCO_3$, $Na^+$, $pO_2$, $CO_2$, and glucose in the perfusate must be balanced before perfusion starts. In the case of using bank CPD donor blood, deranged $K^+$ and $Ca^{++}$ concentrations may not allow for a homeostatic prime. This can be adjusted by haemofiltration using Ringers solution as the rinse. All these values should ideally start within normal physiological ranges and should be monitored by inline continuous blood gas analysis. The primary purpose for the perfusate is to avoid causing tissue edema and to maintain ion homeostasis to preserve cardiac function.

The bi-directional perfusate pumping system enables the apparatus to provide Langendorff perfusion flow through isolated aortic root during the initial resuscitation, stabilization, and maintenance phases, and then to switch the direction of perfusate flow to a "working heart" mode during the pre-transplant assessment phase of the heart's physiological functionality during which time the preload i.e., atrial pressure can be set at a constant level as also can be the afterload i.e., arterial pressure. The control of these parameters is computer-regulated with a very tight control algorithm to ensure that the heart is not over-distended and therefore avoid potential damage. These pressures can be precisely controlled to mimic physiological pressure waveforms during normal heart cycles.

The present system and methods provide functional assessments of both the right ventricle and the left ventricle (current systems and methods only provide limited functional assessments of the left ventricle). In addition to assessing physiological functionality, the present system and methods provide morphologic assessments through echocardiography and angiography. The combination of morphological assessments with assessments of right ventricle and left ventricle functionality based on a combination of load independent indices and load dependent indices greatly improves a clinician's ability to make decisions regarding the suitability of donor hearts for transplantation. Moreover, this will allow targeted treatment of organ dysfunction such that more hearts can be recovered and utilized.

The invention includes all embodiments, modifications and variations substantially as hereinbefore described and with reference to the examples and figures. It will be apparent to persons skilled in the art that a number of variations and modifications can be made without departing from the scope of the invention as defined in the claims Examples of such modifications include the substitution of known equivalents for any aspect of the invention in order to achieve the same result in substantially the same way.

Example 1

Figure 2:
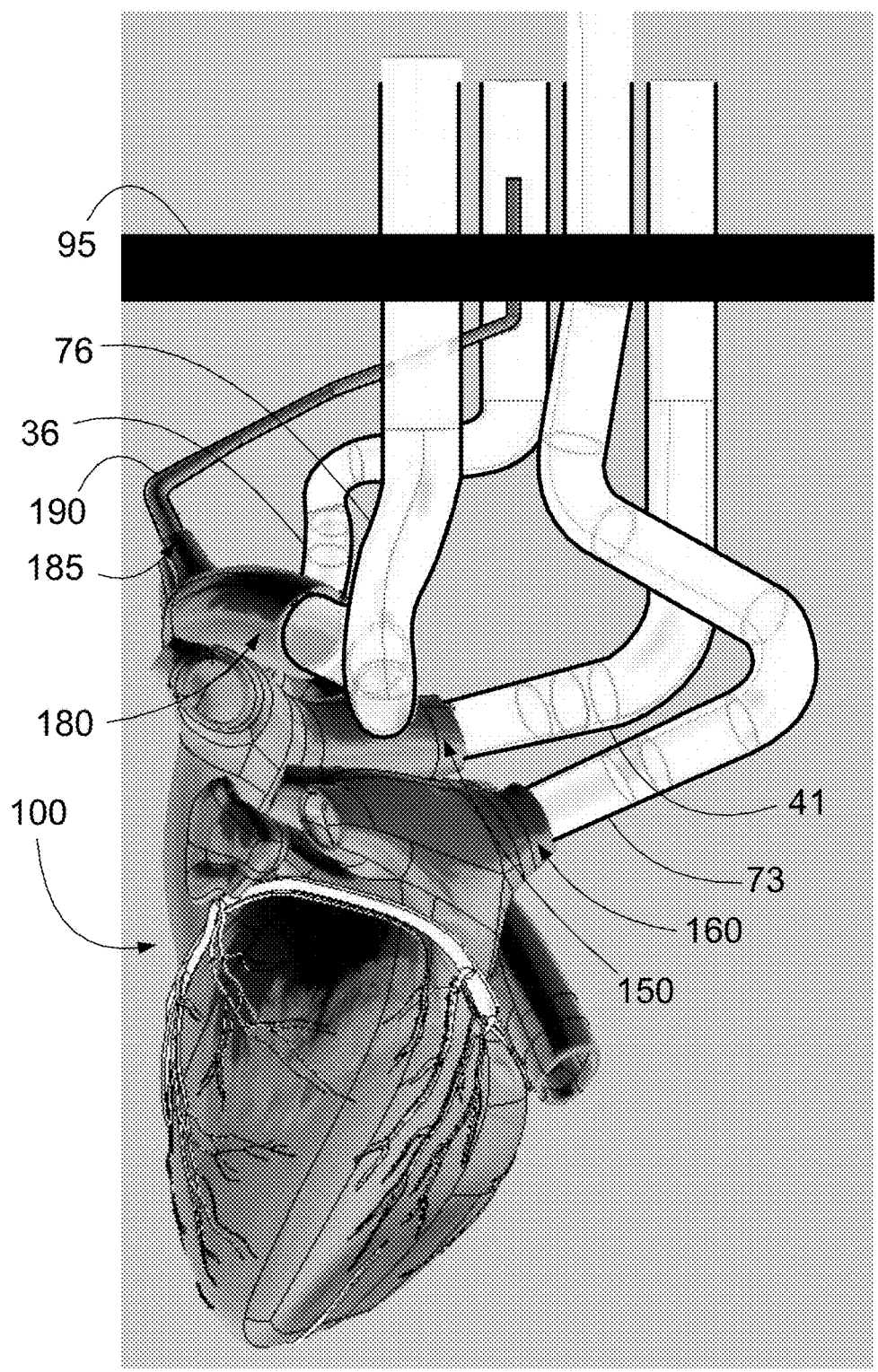
FIG. 2 is a perspective view showing the front of an exemplary excised heart connected to the exemplary apparatus illustrated in FIG. 1.
Figure 3:
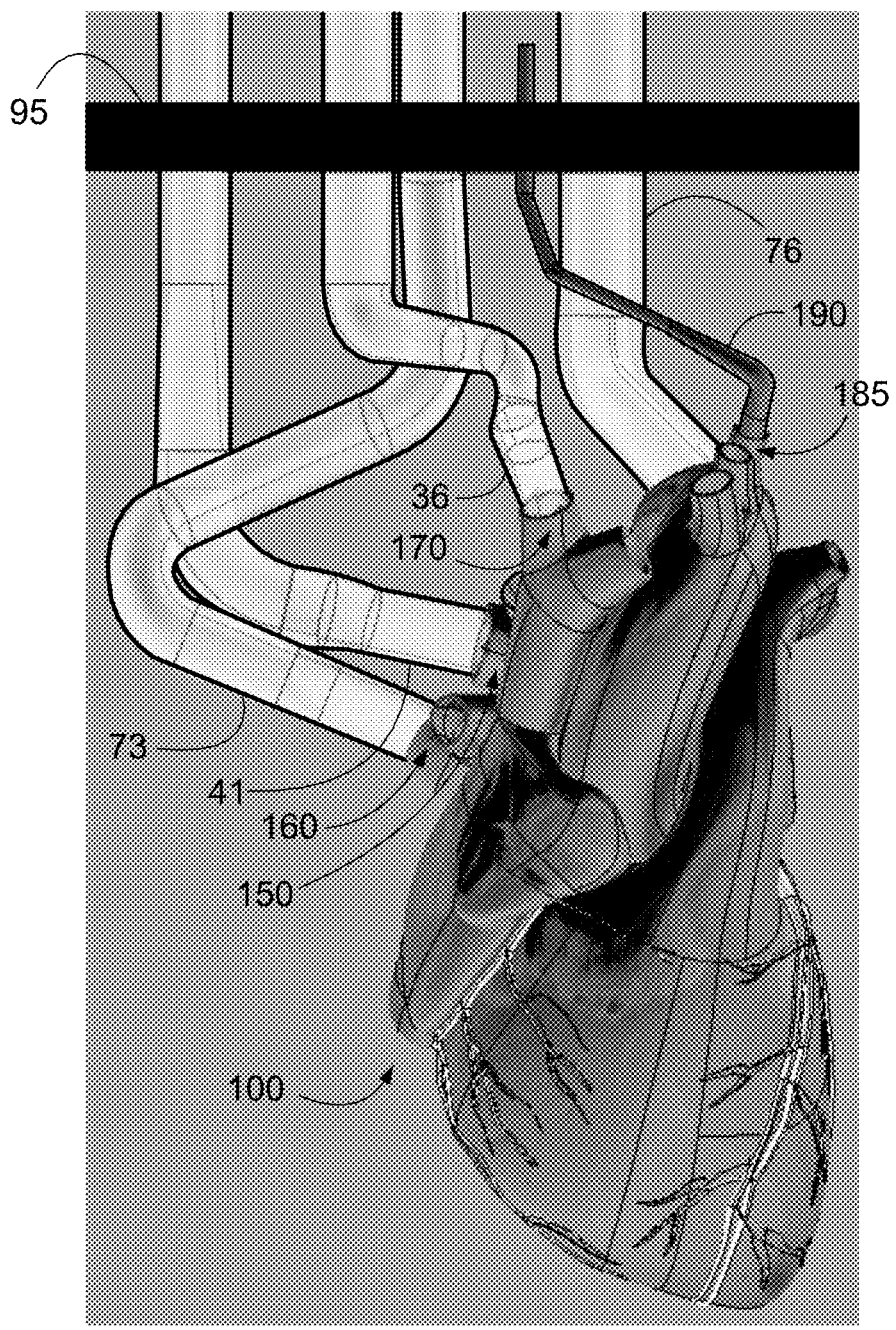
FIG. 3 is a perspective view showing the back of the exemplary excised heart connected to the exemplary apparatus.

An exemplary system 10 according to one embodiment of the present disclosure is shown in FIGS. 1-3. The system comprises:

(1) a perfusion, maintenance, and assessment apparatus comprising a hard-shell container (not shown) housing: (i) a removal support for holding an excised heart, (ii) a soft-shell reservoir 20 for receiving and distributing a perfusate to various entry points in an excised heart 100, and (iii) a lid 95 that is sealably engagable with the heard-shell container;

(2) a perfusate-processing system 30 comprising: (i) a reservoir 31 for receiving egressing perfusate from the perfusion, maintenance, and assessment apparatus and for receiving fresh perfusate, (ii) a roller pump 33, and (iii) a heat-exchanger 35 for adjusting temperature of the perfusate to within the range of about 24° C. to about 35° C., (iv) an oxygenator (not shown but could be a stand-alone machine or alternatively, coupled with the heat exchanger) to condition and balance the perfusate prior to its conveyance to the soft-shell reservoir 20 in the hard-shell container;

(3) a perfusate output pump 40 interconnected with the soft-shell reservoir 20 and the excised heart 100;

(4) an ECG machine 90 connectable to the heart 100 with leads 91 and 92 for monitoring the electrical activity of the heart 100;

(5) monitoring equipment for detecting, recording and/or displaying and/or transmitting load independent indices data (not shown);

(6) monitoring equipment for detecting, recording and/or displaying and/or transmitting load dependent indices data (not shown);

(7) computer equipment for receiving and processing the load independent indices data and the load dependent indices data.

The apparatus lid 95 is provided with a plurality of ports for sealable engaging conduits for interconnecting with various entry points into the heart 100 to enable precisely controllable "working heart" perfusion and Langendorff perfusion. The soft-shell reservoir is fitted with three outlets to: (i) receive oxygenated and heated perfusate from the perfusate-processing system 30 via conduit 38 (also referred to as a cannula); (ii) to preload right atrium via conduits 70 and 76 through the vena cava 180 using pressure delivered by the roller pump 33 of the perfusate-processing system 30; and (iii) receive a flow of perfusate ejected from the left ventricle through the aorta 150 into conduit 41 and then returned to the soft-shell reservoir 20 from the left ventricle under resistance provided i.e, afterload) by pump 40 into lines 27, 27a and 21.

Perfusate egressing the soft-shell reservoir 20 through conduit 70 is split into two flows at juncture 70a, through conduits 76 and 72, that are pressurized by roller pump 33. The perfusate flowing through conduit 76 and ingressing the right atrium through the vena cava 180 flows into right ventricle during "working heart mode" perfusion and then through the pulmonary artery 170 from where it is conveyed by conduit 36 back to the perfusate-processing system 30 for conditioning. During Langendorff perfusion, perfusate flow through conduit 72 is directed into conduit 21 through juncture 21a and then pumped into the aorta 150 via conduit 41 by centrifugal pump 40. The flow pressure from the soft-shell reservoir 20 through conduit 72 is monitored by flow sensor 71, while the flow pressure from the right ventricle into conduit 36 for return to the perfusate-processing system 30 is monitored by flow sensor 37. Integrated pressure ports 28, 42 and 74 monitor and control perfusate pressures at the connection of conduit 21 with the centrifugal pump (i.e., afterload pump) 40, at the connection of conduit 41 with the aorta 150, and at the connection of the line 73 with the pulmonary vein 160, respectively. Clamp 26 on conduit 72 is open during Langendorff perfusion while clamp 25 on line 21 is closed thereby causing the perfusate to be supplied only to the aorta 150 and aortic root, providing coronary blood flow, the effluent emerging from the coronary sinus, collected in the right atrium and returned through the right ventricle and pulmonary artery 170 to the hardshell reservoir 31 through conduit 36. In Langendorff mode, coronary blood flow can be estimated through the flow sensor 37 on conduit 36. During "working heart mode" perfusion, clamp 26 on conduit 72 is closed while clamp 25 on line 21 is open thereby causing the perfusate to cycle from conduit 27 through juncture 72a into conduit 73 for deliver into the left atrium through the pulmonary vein from where in flows into the left ventricle and egresses through the aorta 150 into line 41 and is pumped by the heart to the soft-shell reservoir through conduit 21 with the centrifugal pump 40 supplying tightly regulated afterload.

Figure 4:
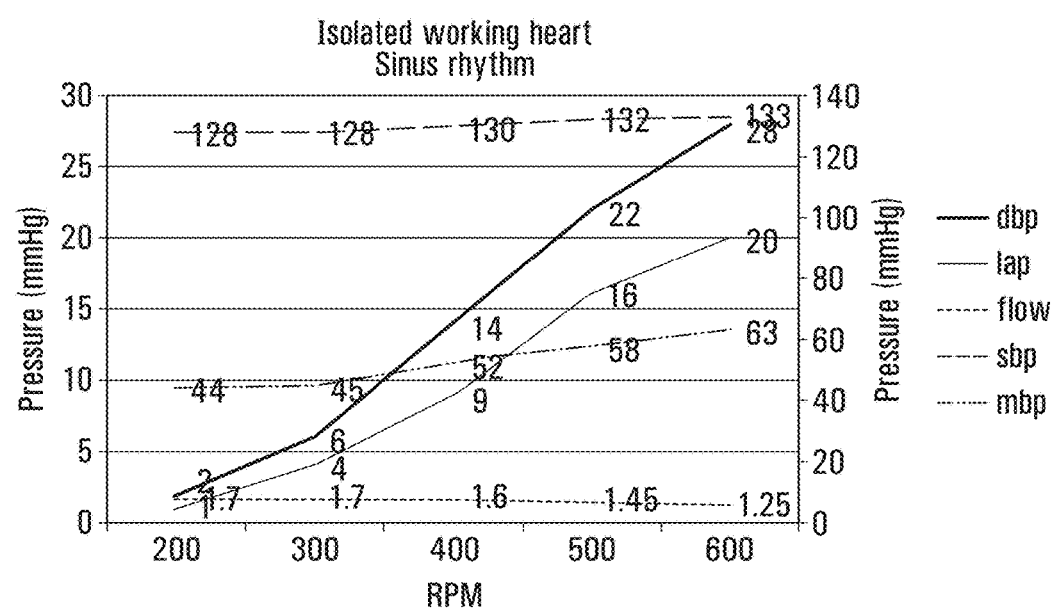
FIG. 4 is a chart showing the effects of increasing pump pressure (RPM) on the following flow pressures of perfusate through an excised heart mounted into the exemplary apparatus: diastolic blood pressure (dbp), left artrial pressure (lap), flow rate of perfusate into the left atrium (flow), systolic blood pressure (sbp), and mean blood pressure (mbp)
Figure 5:
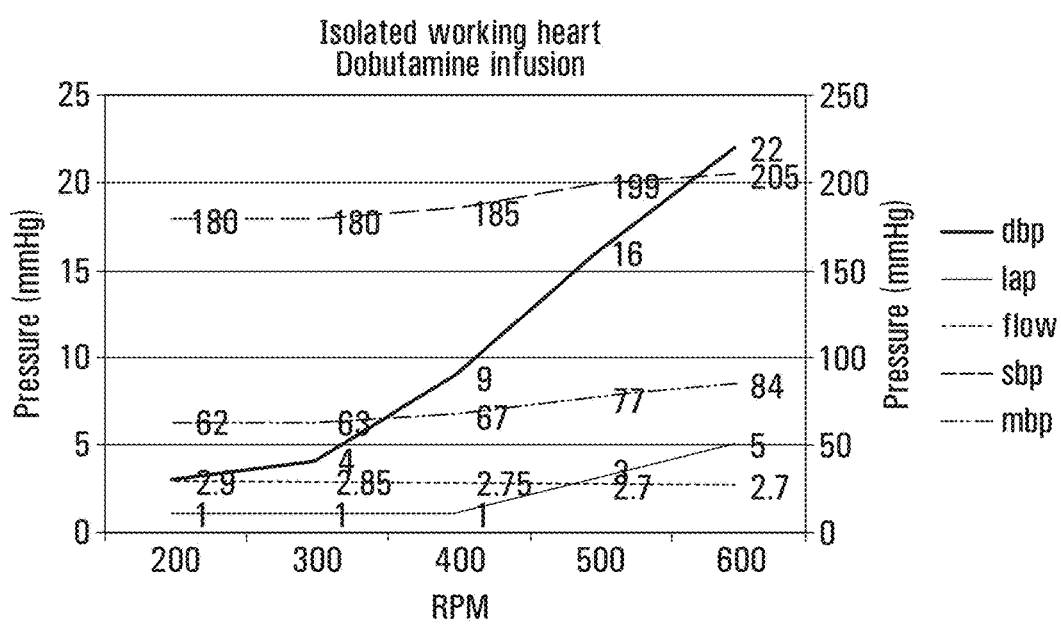
FIG. 5 is a chart showing the effects of dopamine infusion concurrent increasing pump pressure (RPM) on the following flow pressures of perfusate through the excised heart: diastolic blood pressure (dbp), left artrial pressure (lap), flow rate of perfusate into the left atrium (flow), systolic blood pressure (sbp), and mean blood pressure (mbp)

The three pressure sensors 28, 42, 74, the two flow meters 37 and 71, along with the ECG trigger signals augment the computer automation control system for adjusting pump motor speeds, clamp positioning, perfusion system operation, and test modes for the left ventricle. The automation system includes motor speed controllers with feedback, sensor readout hardware and system component synchronization via a personal computer running the computation algorithms During perfusion and maintenance of an excised heart, the heart is secured in the stand in the hard-shell container which is filled with perfusate held at a normothermic temperature to enable for fluoroscopy across the chamber and echocardiography through the saline. Perfusate flows from the pulmonary artery (right ventricle) into the hard-shell reservoir by gravity. Perfusate is roller pumped from this reservoir through an oxygenator with an integrated heater to the soft-shell reservoir (exemplified by Medtronic's Affinity reservoir bag). During Langendorff perfusion and working heart perfusion, the magnetically-coupled centrifugal pump (exemplified by Medtronic's BXP-80 pump) will provide flow to the coronary arteries or resistance to the aorta, respectively. Monitoring of atrial pressure, aortic pressure and flow through the heart during working mode enables assessment of cardiac function while varying resistance to flow (i.e., afterload), as shown in FIG. 4.

Pressure-volume maps of the ventricles are obtained by deploying a pressure wire in a selected ventricle via tubing access ports in the tubing external to the perfusion chamber. Aortic pressure and out-flow profiles are monitored with an additional flow sensor placed on the aortic output conduit 41 to derive a pseudo pressure-volume curve less invasively and on a continuous manner. Similarly, a flow meter placed on the right atrium inflow conduit 76 and a pressure sensor placed onto the right ventricle output conduit 36 enables recording of continuous pseudo pressure-volume graphs.

Echocardiography of the heart is performed through the perfusate-filled perfusion chamber. If required, a block of malleable acoustic-matching gel is matched to the radius of the perfusion chamber to allow for acoustical coupling. There is a risk that sound wave conduction across the polycarbonate perfusion chamber may be insufficient to allow for imaging. Mitigation of this risk may include thinner chamber wall, different wall material or further conduction enhancement. Angiography is performed by placing a guide catheter down the aortic cannula and engaging the ostium of the coronary artery under fluoroscopic guidance. During fluoroscopy, contrast is injected down the guide catheter and perfusate is wasted from the system prior to entering the hard-shell reservoir if the volume of contrast would overload the perfusion system.

Example 2

The study disclosed in this example was conducted at the Institute for Biodiagnostics (NRC, Winnipeg, MB, Canada). The protocol was approved by the local Institutional Animal Care Committee adhering to the guidelines set by the Canadian Council on Animal Care.

Five domestic swine weighing 40-45 kg were obtained from a commercial source and acclimatized in the animal housing facility for one week prior to the study. On the study days, the animals were premedicated intramuscularly, using atropine 0.05 mg/kg, Midazolam 0.4 mg/kg and Ketamine 20 mg/kg Immediately following sedation, general anesthesia was induced using 5% Isoflurane in oxygen via a mask. Xylocaine endotracheal spray was applied to the larynx and swine were endotracheally intubated with 7.5-mm or 8-mm Portex® tubes (Portex is a registered trademark of Smiths Medical ASD Inc., Keane, N.H., USA) and mechanically ventilated. An IV catheter was placed in an ear vein and supplemental fluid (0.9% saline) was administered. During surgery, animals were maintained with 2.0-2.5% isoflurane. Continuous physiological parameters including, ECG, BP, and end-tidal $CO_2$ were monitored (PM-9000 Veterinary Portable Monitor, Mindray Corp, Nanshan, China) and kept within acceptable limits.

Each swine's chest was entered through a midline sternotomy and the heart prepared for retrieval. 300 u/kg heparin was administered at the beginning of the procedure. Donation after circulatory arrest was simulated through initiation of hypoxic cardiac arrest via a cessation of mechanical ventilation. Once the animal arrested, a 15-min stand-off period was observed. Initial myocardial protection was then achieved by infusing 250 ml Plegisol® (Plegisol is a registered trademark of Hospira Inc., Lake Forest, Ill., USA), 4 ml of KCl (1M) and 250 ml autologous blood into the isolated aortic root at 8° C. 50 mg lignocaine were added to the reservoir to prevent fibrillation once ex vivo perfusion was initiated. Long sections of aorta, pulmonary artery and superior vena cava were excised with the heart to ensure adequate space for cannulation with the ex vivo perfusion system. The heart was weighed immediately after removal from the body. The swine was exsanguinated via the thoracic aorta, and 1600 ml of blood was returned to the reservoir of the perfusion system by the pump sucker.

After excision, a flexible cone cannula was sewn to the left atrium and a Xvivo® arterial cannula (Xvivo is a registered trademark of Xvivo Perfusion AB, Gothenburg, Sweden) was inserted into the ascending aorta. Cannulae with ⅜" connectors were secured to each of the superior vena cava, pulmonary artery, the inferior vena cava, and were oversewn. The heart was transferred onto the perfusion rig where all cannulae were secured to ⅜" PVC tubing. The heart was suspended within a large funnel with an attached upper splashguard. Securing clamps attached to the mast of the rig stabilized all lines, leaving the heart unrestricted on all sides (FIGS. 2, 3). Biomedicus flow probes (Bio-Probe DP38, Medtronic Inc., Minneapolis, Minn., USA) were inserted in the left atrium line and right atrium line.

The saline prime was displaced with swine blood to leave a blood prime with a haematocrit of 20-24%. Sodium bicarbonate and glucose were added to bring the prime within normal physiological blood ranges. After cannulation, the heart was de-aired by atrial filling from the venous bag and an air-free connection was made to the circuit. Perfusion was started after an average 18±6 minutes from the time of cardioplegia delivery in the donor. Retrograde Langendorff perfusion was commenced at 300-500 ml/min with a pressure of 50-60 mmHg from the centrifugal pump to achieve the coronary blood flow. The venous blood from the coronary sinus was returned to the hard-shell venous reservoir via the pulmonary artery line. An air inlet line was inserted into the pulmonary artery via a ⅜" Y-connector to prevent a siphon effect. Sweep gas flow was adjusted to a $FiO_2$=0.6, 100-200 ml/min $O_2$ and 10-15 ml/min $CO_2$ achieved sufficient gas exchange Left atrial, right atrial, aortic and pulmonary arterial pressures were continuously monitored by recording diastolic blood pressure (dbp), left arterial pressure (lap), flow rate of perfusate into the left atrium (flow), systolic blood pressure (sbp), and mean blood pressure (mbp). If ventricular fibrillation was required, the heart was defibrillated with 10 joules.

Figure 7:
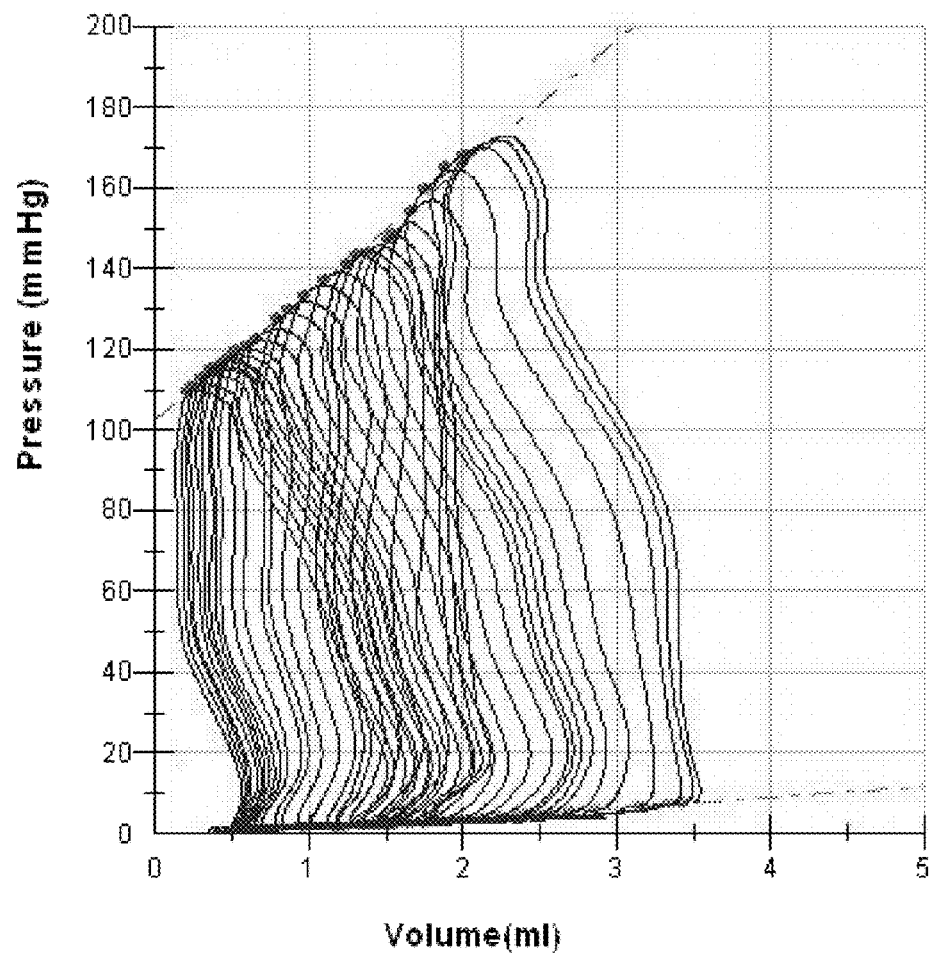
FIG. 7 is a chart showing a family of pressure/volume loops obtained from the left ventricle during the study of the effects of dopamine infusion concurrent with increasing perfusate flow pressures shown in FIG. 5.

After 15 min of stable Langendorff perfusion, biventricular preload was instituted gradually. As the heart started to eject against the retrograde flow the centrifugal pump speed was reduced to 100-200 rpm, which provided afterload to the ejecting left ventricle (FIG. 4). As preload was increased by releasing the roller clamps, biventricular output increased and afterload was adjusted to provide diastolic pressure (FIG. 4). When measurements with the Biomedicus flow probes indicated that the heart was ejecting, a Ventri-Cath multisegment 8-electrode combined pressure/volume catheter (Millar Instruments Inc., Houston, Tex., USA) was inserted along the longitudinal axis of the left ventricle with the proximal electrode at the level of the aortic valve. In similar fashion, another catheter was inserted into the right ventricle via the pulmonary artery. Data was collected at a sampling rate of 200 Hz with Lab chart 7 (AD Instruments, Bella Vista, NSW, Australia), using a Powerlab AD module. A family of pressure/volume loops was obtained by manually compressing the left atrial inflow or the right atrial inflow. Subsequently, a dobutamine infusion was started at 2.5 ug/Kg/min to 5 ug/kg/min) to allow assessment of contractile reserve and a new set of pressure/volume loops was generated in the same way as before (FIG. 7).

Figure 6:
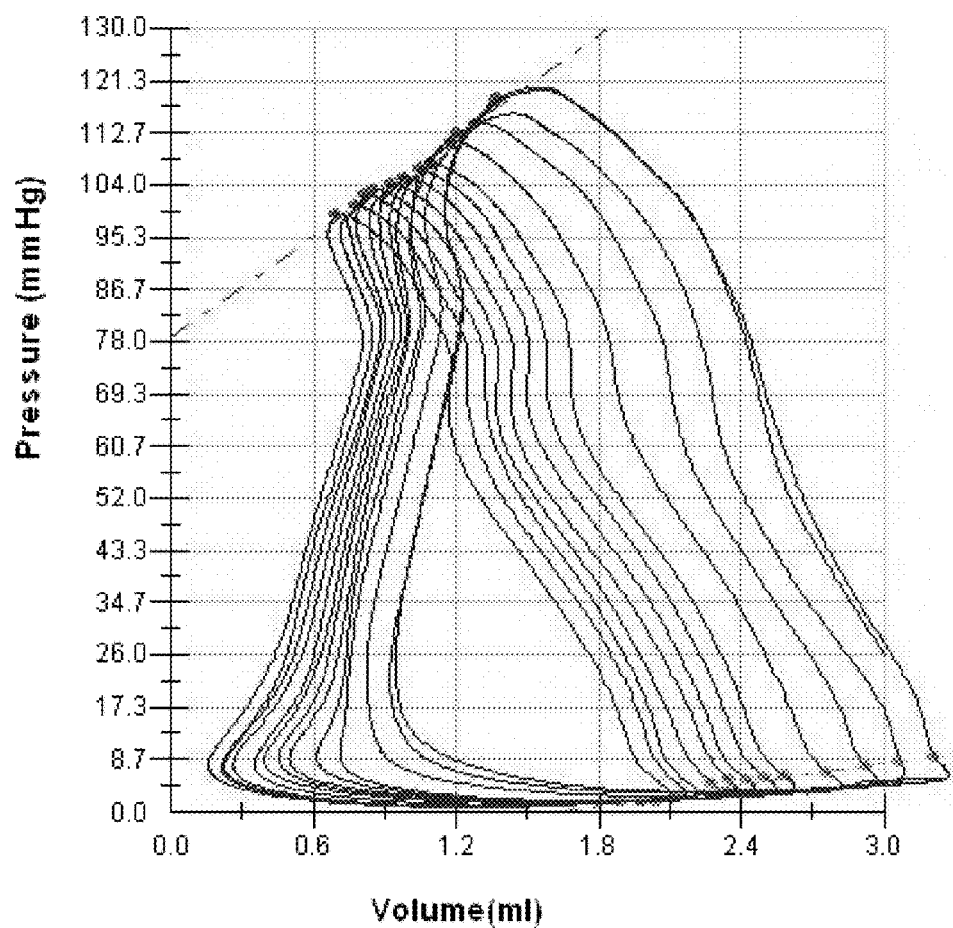
FIG. 6 is a chart showing a family of pressure/volume loops obtained from the left ventricle during the study of the effects of increasing perfusate flow pressures shown in FIG. 5.
Figure 8:
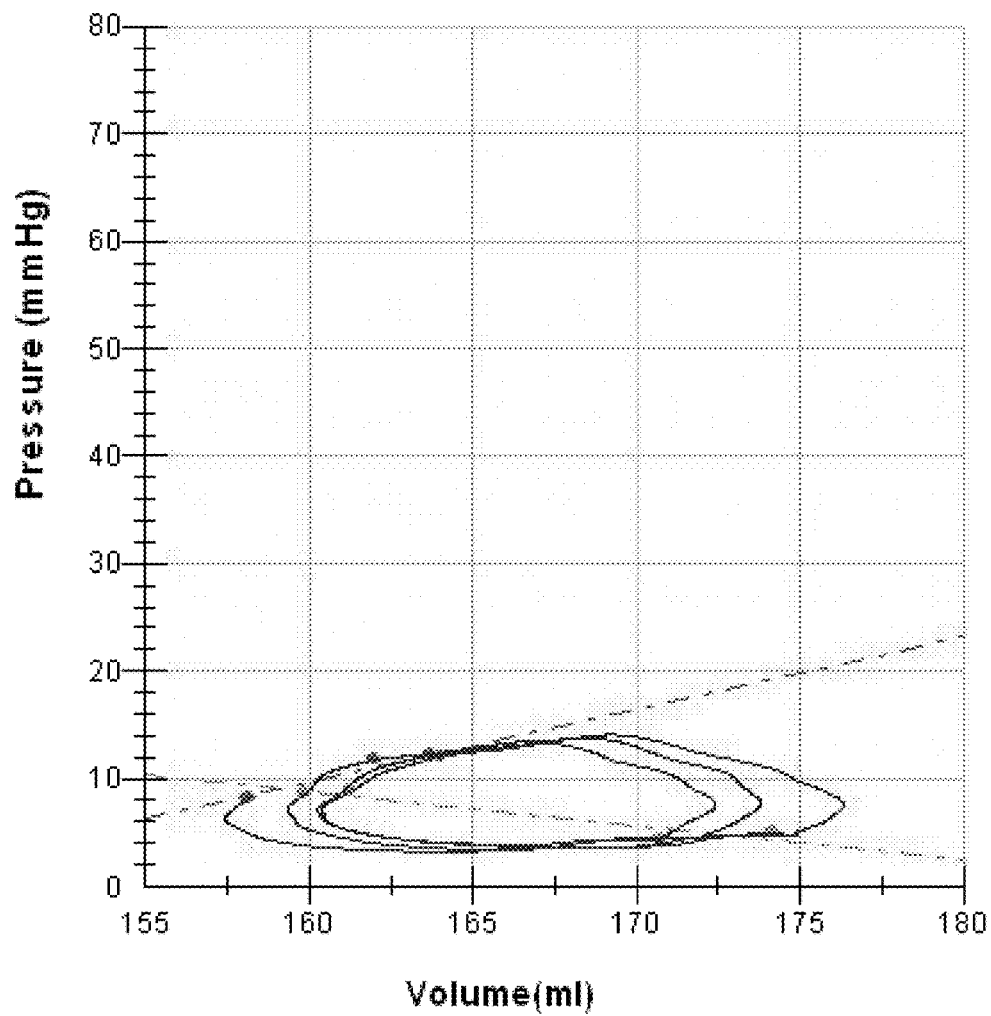
FIG. 8 is a chart showing a family of pressure/volume loops obtained from the right ventricle during the study of the effects of increasing perfusate flow pressures shown in FIG. 5.
Figure 9:
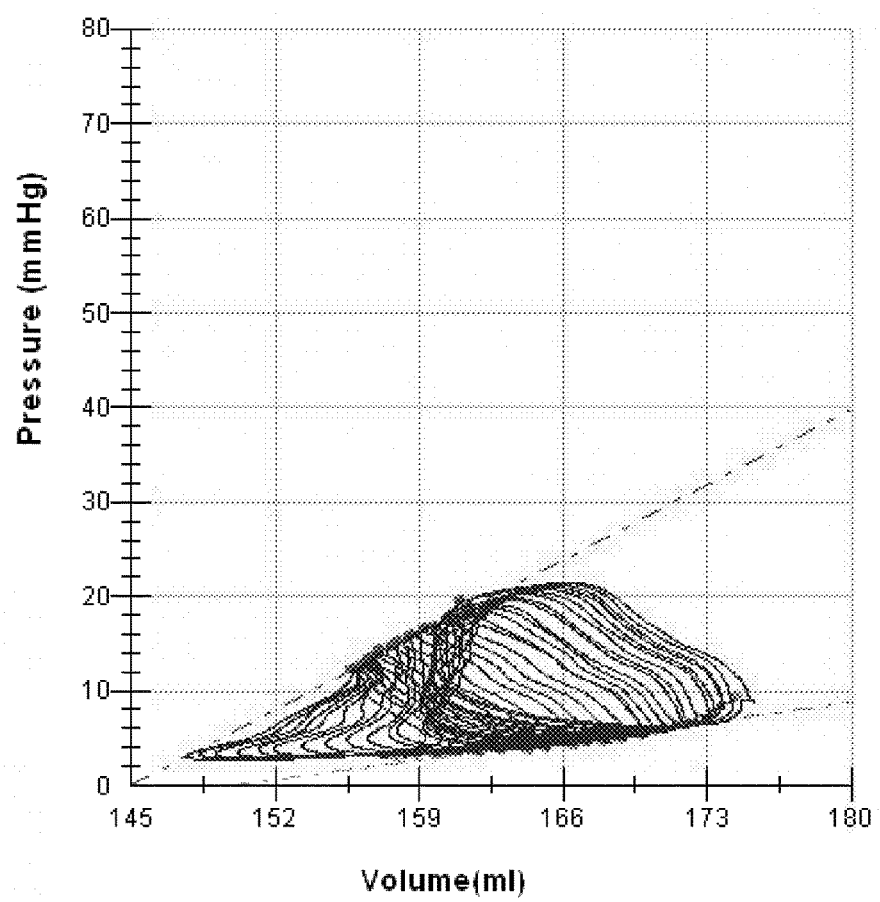
FIG. 9 is a chart showing a family of pressure/volume loops obtained from the right ventricle during the study of the effects of dopamine infusion concurrent with increasing perfusate flow pressures shown in FIG. 5.

During 5 h of perfusion, the physiological variables of the perfusate were kept within normal limits. During the working mode, the left ventricular end systolic pressure volume relationship (LV ESPVR) was 23.1+/−11.1 and the left ventricular preload recruitable stroke work relationship (LV PRSW) was 67.8+/−7.2 (FIG. 6). Both measures increased significantly after infusion of dobutamine. The LV ESPVR increased to 45.1+/−12.2, p=0.01, while the LV PRSW increased to 102.5+/−18.2, p=0.03 (FIG. 7). The right ventricular end systolic pressure volume relationship (RV ESPVR) and the right ventricular preload recruitable stroke work relationship (RV PRSW) were also measured in 2 animals (FIG. 8). The RV ESPVR increased from 4.1+/−2.3 to 11.9+/−4.1 after dobutamine infusion, while the RV PRSW increased from 6.7+/−2.4 to 8.7+/−4.6 after dobutamine infusion (FIG. 9).

The resuscitated hearts displayed significant upward and leftward shifts of their LV ESPVR and RV ESPVR, significant increases in their LV PRSW and RV PRSW, and minimal stiffness. Two hearts regained sinus rhythm after reperfusion, whilst the remaining three required defibrillation. Small boluses of sodium bicarbonate, and glucose were the only drugs added by the research technician.

The circuit was effective during reperfusion and working modes whilst proving to be successful in maintaining cardiac function in excess of five hours. The use of the Biomedicus pump in delivering Langendorff flow and providing afterload to the working heart was simple and effective. Diastolic pressures could be effectively manipulated with instant cardiac response to increased coronary perfusion in the working phase. The venous bag provided suitable and effective preloads to the left atrium and the right atrium, and these could be easily adjusted when either atria started to stretch.

The conductance catheter was simply inserted via purse strings around the innominate artery and PA, but on several occasions became restricted by the ventricular trabeculae. Nevertheless, shapes of the captured PV loops were outstanding in this model. There was no evidence of thrombi in the circuits at washout. Blood gases stayed very stable with only small additions of glucose and sodium bicarbonate without any noticeable rise in serum lactate.

Figure 10:
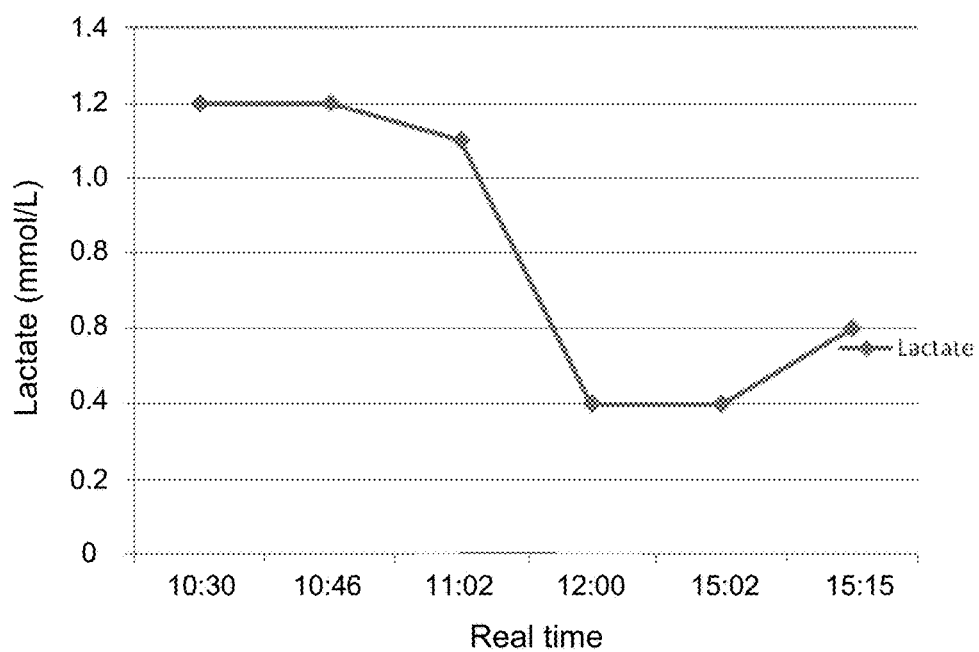
FIG. 10 is a chart showing the changes in lactate concentrations in the excised heart during the study shown in FIG. 4.
Figure 11:
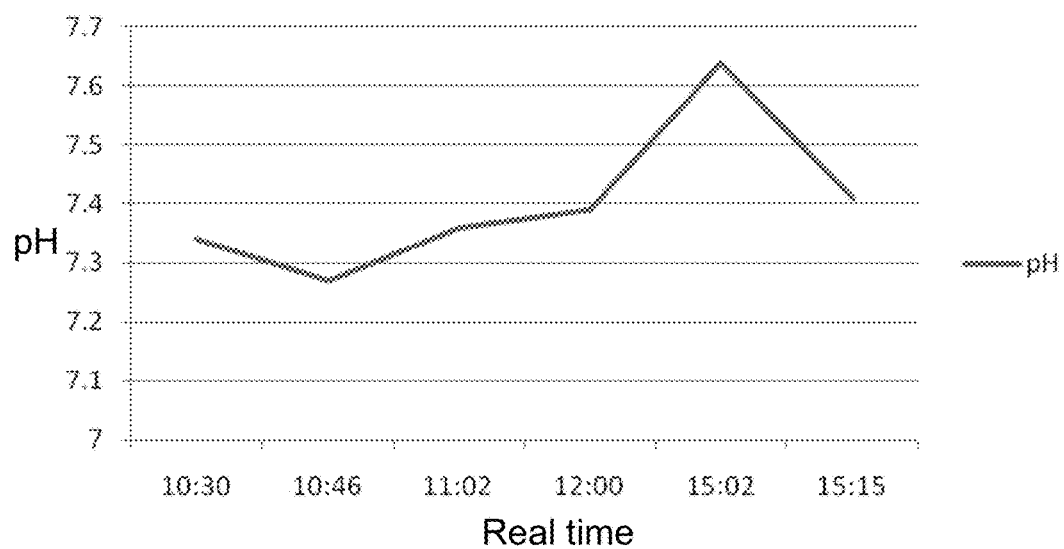
FIG. 11 is a chart showing the changes in the pH in the excised heart during the study shown in FIG. 4.

After 5 h, the heart was removed from the rig, weighed, dissected and biopsies were taken. Standard PVAN analysis software (Millar Instruments, Houston, Tex., USA) was used for data analysis (FIGS. 10, 11).

Example 3

Figure 12:
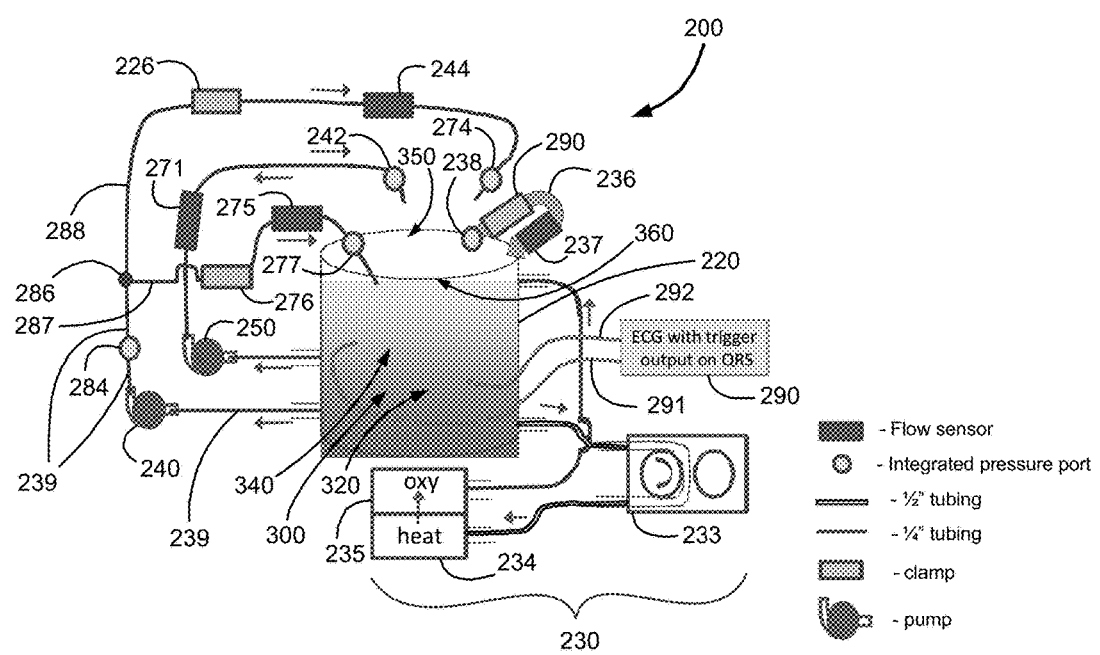
FIG. 12 is a schematic illustration of an exemplary testing, assessment, and maintenance apparatus for harvested donor hearts according to another embodiment of the present disclosure.

An exemplary system 200 according to an embodiment of the present disclosure for maintenance and monitoring of harvested organs is shown in FIG. 12. The harvested organ maintenance and monitoring system 200 comprises:
(1) a organ maintenance and perfusion apparatus comprising
a hard-shell container 220 housing a removal support (not shown) for mounting thereon an excised heart 300, and a lid that is sealably engagable with the hard-shell container 220. The hard-shell container 220 also serves as a reservoir for a perfusate solution to enable total immersion, bathing and perfusion of an excised heart 300 mounted into the removable support;

(2) a perfusate processing system 230 comprising: (i) a pump 233 for circulating the perfusate solution from the hard-shell container 220 through (ii) a heat-exchanger 234 for adjusting temperature of the perfusate to within the range of about 24° C. to about 35° C., and (iii) an oxygenator 235 to condition and balance oxygen content of the perfusate solution prior to its conveyance back into to the hard-shell container 220;

(3) a perfusate preloading pump 240 interconnected to the hard-shell container 220 for providing a flow of the perfusate solution into the left atrium and the right atrium delivered through an integrated pressure port 284 and then split into two lines 287, 288 by a "Y" connecter 286, with line 87 delivering the perfusate solution into the right atrium and line 288 delivering the perfusate solution into the left atrium;

(4) a perfusate afterloading pump 250 interconnected to the hard-shell container 220 for providing a flow of the perfusate solution into the aorta 350;

(5) an ECG machine 290 connectable to the heart 300 with leads 291 and 292 for monitoring the electrical activity of the heart 300;

(6) monitoring equipment for detecting, recording and/or displaying and/or transmitting load independent indices data (not shown);

(7) monitoring equipment for detecting, recording and/or displaying and/or transmitting load dependent indices data (not shown);

(8) computer equipment (not shown) for receiving and processing the load independent indices data and the load dependent indices data.

The apparatus lid is provided with a plurality of ports for sealably engaging conduits for interconnecting with various entry points into the heart 300 to enable precisely controllable "working heart" perfusion and Langendorff perfusion.

The hard-shell container 220 is provided with at least four ports. Two of the ports are interconnected to a conduit infrastructure for conveyance of a flow of the perfusate solution from the hard-shell container 220 through the heat-exchanger 234 and oxygenator 235 and then back into the hard-shell container 220 by pressure provided by pump 233.

Another of the ports interconnects the hard-shell container 220 with the perfusate preloading pump 240. The perfusate preloading pump 240 provides a controllable pressurized flow of perfusate solution from the hard-shell container 220 into the right atrium via line 287 left atrium via line 288. The integrated pressure port 284 interposed the perfusate preloading pump 240 and the Y connecter 286, communicates with and cooperates with the computer equipment for controllably regulating pressurized output of perfusate solution from the perfusate preloading pump 240.

A flow sensor 275 is interposed line 287 to enable electronic monitoring of the flow rate of the perfusate solution delivered from the perfusate preloading pump 240. A servo-actuated partial occlusion clamp 276 is interposed in line 287 between the flow sensor 275 and the Y connector 286 for regulating perfusate solution flow and pressure delivered into the right atrium. A pressure port 277 is interposed the flow sensor 275 and the right atrium to monitor and communicate the flow rate and/or pressure of perfusate solution delivered into the right atrium by line 287. The flow sensor 275, clamp 276, and pressure port 277 communicate with and cooperate with the computer equipment for adjusting and controlling the flow rates of the perfusate solution from the perfusate preloading pump 240 into the right atrium.

A flow sensor 244 is interposed line 288 to enable electronic monitoring of the flow rate of the perfusate solution delivered from the perfusate preloading pump 240. A servo-actuated partial occlusion clamp 226 is interposed in line 288 between the flow sensor 244 and the Y connector 286 for regulating perfusate solution flow and pressure delivered into the left atrium. A pressure port 274 is interposed the flow sensor 244 and the left atrium to monitor and communicate the flow rate and/or pressure of perfusate solution delivered into the left atrium by line 288. The flow sensor 244, clamp 226, and pressure port 274 communicate with and cooperate with the computer equipment for adjusting and controlling the flow rates of the perfusate solution from the perfusate preloading pump 250 into the left atrium.

Another of the ports interconnects the hard-shell container 220 with a conduit infrastructure that is connectable to the aorta 350 of the heart 300 for maintenance of, monitoring of, and assessing of the functioning of the left ventricle of the heart 300. Pressurized flow of perfusate solution through this conduit infrastructure is controllably regulated by an after-loading pump 250, a flow sensor 271, and a pressure port 242 interposed the hard-shell container 220 and the aorta 350. The after-loading pump 250, the flow sensor 271, and the pressure port 242 communicate with, and cooperate with the computer equipment for adjusting and controlling the flow rates of the perfusate solution flowing through the conduit infrastructure.

During "working heart mode" perfusion, the perfusate solution is pumped into the heart 300 by the preloading pump 240 via lines 287, 288 into the right atrium and the left atrium respectfully. The perfusate solution is then transferred into the right ventricle 340 and then egresses through the pulmonary artery 360 through conduit 236 back into the reservoir of the hard-shell container 220. The flow rate and pressure of the perfusate solution through pressure port 238 into conduit 236 wherein the flow rate and pressure of the perfusate solution is monitored by flow meter 237 and regulated by clamp 239. The perfusate solution ingressing the left atrium via line 288 is transferred into the left ventricle 320 and then egresses through the aorta 350 into the conduit infrastructure through pressure port 242, flow sensor 271, after-loading pump 250 and then into the hard-shell container 220.

During Langendorff perfusion, the flow of perfusate solution is directed from the hard-shell container 220 into the conduit infrastructure through after-loading pump 250, flow sensor 271, pressure port 242, and then into the aorta and the aortic root. The perfusate solution effluent flows through the coronary sinus into the right atrium, then into the right ventricle and eggresses through the pulmonary artery 360 to the hard-shell container 220 through conduit 236. In Langendorff mode, coronary blood flow can be estimated through the flow sensor 237 on conduit 236.

The four pressure sensors 275, 244, 237, and 271, the three clamps 226, 276, along with the ECG⁻ trigger signals augment the computer automation control system for adjusting pump motor speeds, clamp positioning, perfusion system operation, and test modes for the left ventricle. The automation system includes motor speed controllers with feedback, sensor readout hardware and system component synchronization via a personal computer running the computation algorithms. During perfusion and maintenance of an excised heart 300, the heart is secured in the stand (not shown) in the hard-shell container 220 which is filled with perfusate solution held at a normothermic temperature to enable for fluoroscopy across the chamber and echocardiography through the saline. Perfusate solution flows from the pulmonary artery (right ventricle) into the hard-shell reservoir under pressure provided by the perfusate preloading pump 240. The perfusate solution is pumped from the hard-shell container 220 by pump 233 through a heat-exchanger 234 and an oxygenator 235 and then back to the hard-shell container 220.

Pressure-volume maps of the ventricles are obtained by deploying a pressure wire in a selected ventricle via tubing access ports in the tubing external to the perfusion chamber. Aortic pressure and out-flow profiles are monitored with an additional flow sensor placed on the aortic output conduit 41 to derive a pseudo pressure-volume curve less invasively and on a continuous manner. Similarly, a flow meter placed on the right atrium inflow conduit 76 and a pressure sensor placed onto the right ventricle output conduit 36 enables recording of continuous pseudo pressure-volume graphs.

Echocardiography of the heart is performed through the perfusate-filled perfusion chamber. If required, a block of malleable acoustic-matching gel is matched to the radius of the perfusion chamber to allow for acoustical coupling.

There is a risk that sound wave conduction across the polycarbonate perfusion chamber may be insufficient to allow for imaging. Mitigation of this risk may include thinner chamber wall, different wall material or further conduction enhancement. Angiography is performed by placing a guide catheter down the aortic cannula and engaging the ostium of the coronary artery under fluoroscopic guidance. During fluoroscopy, contrast is injected down the guide catheter and perfusate is wasted from the system prior to entering the hard-shell reservoir if the volume of contrast would overload the perfusion system.

The invention claimed is:

1. An apparatus for perfusing excised donor hearts, comprising:
   a support for supporting an excised donor heart;
   a plurality of conduits for connecting a reservoir of a perfusate to the heart supported on the support to circulate the perfusate through the heart, said conduits comprising a first cannula for cannulation into an atrium of the heart, and a second cannula for cannulation into an aorta of the heart;
   a servo-actuated partial occlusion clamp connected to the first cannula for automated control of a fluid flow through the first cannula;
   an afterload pump in fluid communication with said second cannula, said afterload pump configured and operable to selectively apply an afterload pressure to the aorta to resist circulation of the perfusate through the heart when said clamp is opened to allow the perfusate to enter the atrium through said first cannula; and
   a controller in electronic communication with said clamp and said afterload pump, and configured to automatically control operation of said clamp and said afterload pump for regulating circulation of the perfusate through the heart.

2. The apparatus of claim 1, wherein said pump is a centrifugal pump.

3. The apparatus of claim 1, wherein the pump is a first pump, and said apparatus comprises a second pump in fluid communication with the atrium through said clamp, for applying a fluid pressure to the atrium.

4. The apparatus of claim 3, wherein said second pump is a centrifugal pump.

5. The apparatus of claim 1, wherein said atrium is the right atrium of the heart.

6. The apparatus of claim 1, wherein said controller comprises a microprocessor.

7. The apparatus of claim 1, comprising a plurality of flow regulating devices positioned for adjusting perfusate flows in selected ones of said conduits.

8. The apparatus of claim 1, comprising a temperature sensor positioned for detecting a temperature of the perfusate, and comprising a heat-exchanger for adjusting the temperature of the perfusate.

9. The apparatus of claim 1, comprising flow sensors positioned for detecting flow rates in selected ones of said conduits.

10. The apparatus of claim 1, comprising a first pressure sensor positioned for detecting the afterload pressure, and a second pressure sensor positioned for detecting the preload pressure.

11. The apparatus of claim 1, comprising an oxygenator for controllably adjusting an oxygen content of the perfusate.

12. The apparatus of claim 1, comprising said reservoir.

13. The apparatus of claim 1, comprising an electrocardiographic device.

14. The apparatus of claim 1, comprising a hard-shell container sealingly engagable with the reservoir, wherein said support is removably mounted in the hard-shell container.

15. The apparatus of claim 14, wherein the reservoir comprises a soft-shell reservoir housed in said hard-shell container, said soft-shell reservoir comprising ports for sealingly engaging and communicating with selected ones of said plurality of conduits.

16. The apparatus of claim 14, comprising a lid sealably engagable with the hard-shell container, said lid comprising ports for sealably engaging said first cannula and said second cannula.

17. The apparatus of claim 1, wherein said plurality of conduits comprise a resilient conduit connected to said first cannula, and said clamp clamps around said resilient conduit for regulating flow of the perfusate through said resilient conduit.

18. The apparatus of claim 1, wherein said plurality of conduits comprises a cannula for cannulation into a pulmonary vein of the heart.

* * * * *